United States Patent [19]
Arabeyre et al.

[11] Patent Number: 5,497,513
[45] Date of Patent: Mar. 12, 1996

[54] REMEDIAL SUPPORT APPLIANCE FOR MEDICAL USE ON A LEG OR AN ARM

[75] Inventors: Françoise Arabeyre; René Arabeyre, both of Chatellerault, France

[73] Assignee: Cognon-Morin, Chatellerault, France

[21] Appl. No.: 219,379

[22] Filed: Mar. 29, 1994

[30] Foreign Application Priority Data

Apr. 2, 1993 [FR] France .................................. 93 03904

[51] Int. Cl.⁶ .................................................. A61F 13/08
[52] U.S. Cl. .............................. 2/240; 2/16; 2/22; 602/63
[58] Field of Search .......................... 2/239, 240, DIG. 9, 2/16, 22, 311, 320, 409; 66/178 A, 178 R, 172 E; 602/1, 60, 62–65, 75–77

[56] References Cited

U.S. PATENT DOCUMENTS

| | | | |
|---|---|---|---|
| 2,084,938 | 6/1937 | Busch et al. | 2/240 |
| 2,425,479 | 8/1947 | Le Blanc | 2/240 |
| 2,809,673 | 10/1957 | McMurray | 2/DIG. 9 |
| 3,800,331 | 2/1974 | Taddeo | 2/240 |
| 4,048,818 | 9/1977 | Cueman | 66/178 A |
| 4,106,313 | 8/1978 | Boe | 66/178 A |
| 4,172,456 | 10/1979 | Zens | 2/240 |
| 4,180,065 | 12/1979 | Bowen | 2/239 |
| 4,561,267 | 12/1985 | Wilkinson et al. | 66/178 A |

FOREIGN PATENT DOCUMENTS

| | | |
|---|---|---|
| 2302054 | 2/1975 | France . |
| 8217651 | 9/1982 | Germany . |

Primary Examiner—Amy B. Vanatta
Attorney, Agent, or Firm—Sixbey, Friedman, Leedom & Ferguson; Gerald J. Ferguson, Jr.; David S. Safran

[57] ABSTRACT

The invention relates to a remedial support appliance for medical use, comprising an elasticated knit main portion for compressing a leg or an arm in order to treat venous or lymphatic insufficiency. According to the invention, the main portion is extended upwards by an elasticated garter band constituted by an elasticated lace or braid covered on the inside with a pattern made of an antislip material, the fibers constituting the braid or the lace of said band being selected in such a manner that the band presents an elongation characteristic of shallow slope and simultaneously exerts pressure on the limb concerned that is less than the pressure exerted thereon by the main portion of the appliance in the vicinity of said band.

12 Claims, 1 Drawing Sheet

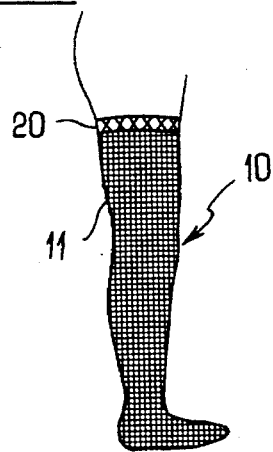
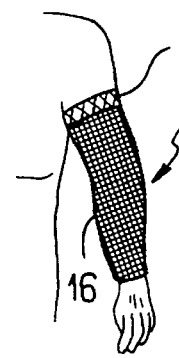
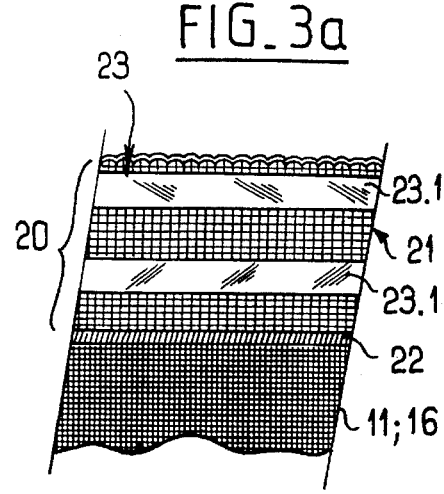
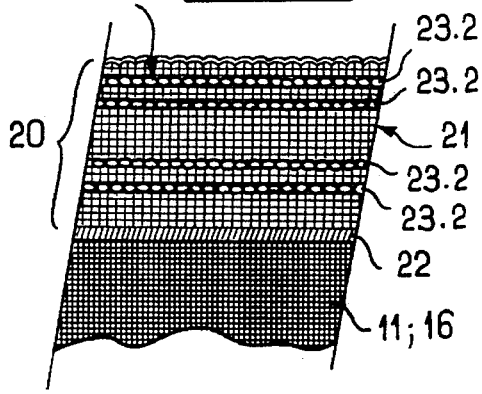
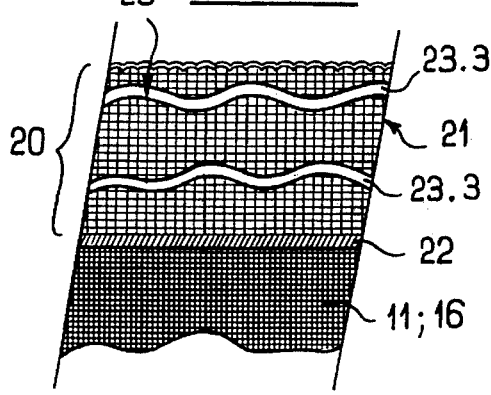
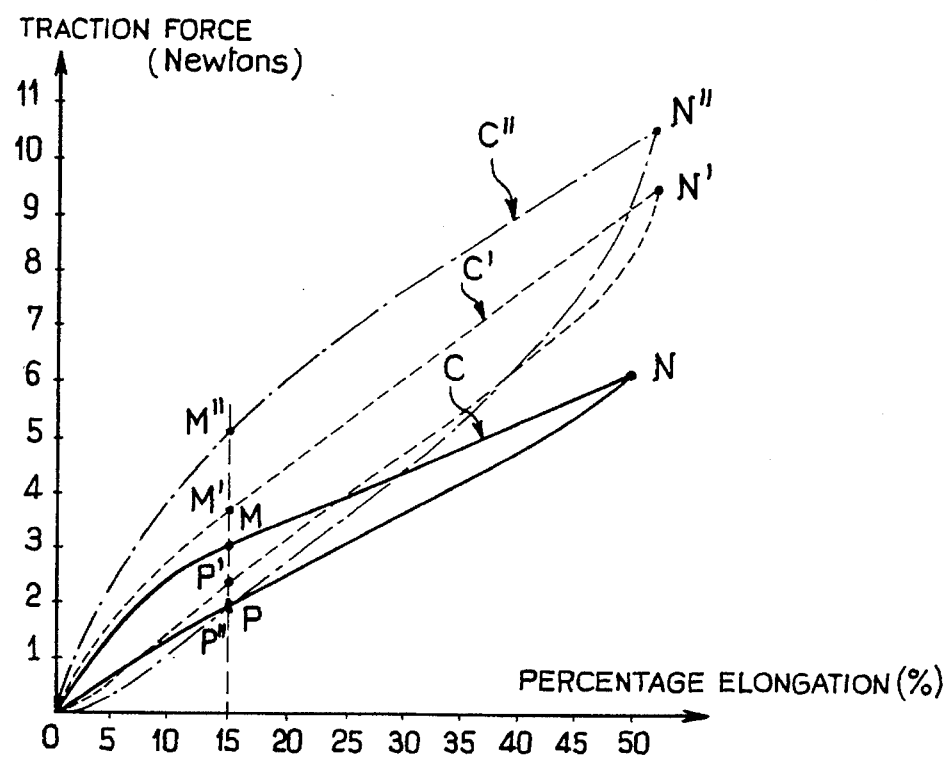

REMEDIAL SUPPORT APPLIANCE FOR MEDICAL USE ON A LEG OR AN ARM

The invention relates to remedial support appliances for medical use on a leg or an arm, the appliances being of a type comprising a main portion of elasticated i.e., elasticized knit that serves to compress the limb on which the appliance is worn in order to treat venous or lymphatic insufficiency by exerting pressure that is degressive from the bottom towards the top of the appliance.

BACKGROUND OF THE INVENTION

Depending on the type of insufficiency concerned (ulcer, varicose veins, edema, phlebitis, lymphoedema) and the part of the patient's body that is affected thereby, it is common practice on a leg to use a stocking, a long sock, or a short sock, and on an arm to use a sleeve whose length varies according to circumstances, the sleeve optionally being fitted with a shoulder strap.

The state of the art is illustrated by the following documents: FR-A-2 671 485, FR-A-2 654 925, FR-A-2 588 890, FR-A-2 587 617 and CH-A-675 201.

In addition to the therapeutic effect produced by applying compression to the limb concerned, such various remedial support appliances must be as tolerable as possible by the patient.

It has been observed that patients already traumatized by the state in which they find themselves actually wear prescribed remedial support appliances on a regular basis only when they are sufficiently comfortable, with the sensation of comfort being both physiological (e.g. in the event of the appliance slipping down and/or creasing) and psychological (the traumatic aspect of fastening means that are bulky and/or complicated).

The problem of the appliance slipping down progressively is particularly important, not only because such slippage is disagreeable for the patient (physiologically because it feels uncomfortable, and psychologically because it looks unattractive), but also because its therapeutic effect is reduced under such circumstances.

In the particular case of elastic stockings (when the patient cannot or will not wear elastic tights), it is present practice to use fastening and support means derived from traditional underwear (e.g. suspenders), or else adhesive means. Suspenders or braces are indeed effective, but in addition to being outdated, such systems remain constraining, uncomfortable, and visible through fitted clothing. Adhesive applied directly to the skin, even when washable in water, is difficult for patients to accept both for physical reasons and for psychological reasons that will readily be understood.

For sleeves designed to treat edema of the arm, particularly in the context of breast surgery and/or cobalt therapy, it is conventional to use a fastening system that includes a strap passing beneath a breast to be fastened on the side, and this often has a traumatic effect on people already shocked by the treatment to which they have been subjected.

It might be tempting to look for inspiration in the antislip systems that are to be found in hosiery for everyday stockings, which are based on the principle of a tight top band that is covered on the inside with one or two circumferential lines of silicone.

In hosiery stockings fitted with such an antislip band, the top band used is elasticated and its component fibers are selected so that said band exerts pressure on the thigh that is very much greater (generally at least three or four times greater) than the very low pressure that is exerted by the stocking proper: since medical elastic stockings are designed to improve return circulation, there can be no question of using a top band designed in that way since that would constitute a kind of tourniquet around the upper thigh specifically at the level of the saphenous vein. In addition, the antislip system based on an elasticated band and used for hosiery stockings generally presents an elongation characteristic having a steep slope, e.g. corresponding to 5% to 7% elongation per Newton exerted in traction, thereby giving rise to large variations in exerted pressure for a given size of stocking depending on the circumference of the thigh: this also goes against the effect that is required of an elastic stocking where it is absolutely essential to avoid any risk of strangulation of the limb concerned.

As a result, the teaching of hosiery stockings appears, a priori, to be of no help in solving the problem posed.

Such attempts may be illustrated by the three following documents.

Document DE-U-82 17 651 describes an elastic stocking whose main portion is extended upwards by an elasticated garter band. The garter band is implemented in the form of a tape made on a crochet machine and covered on its inside with antislip segments or stitches provided in discontinuous manner. Provision is made firstly for the tape to have the same elongation characteristic as the main portion of the stocking in the vicinity of said tape, and thus a characteristic of steep slope (in a diagram where traction force is shown as a function of percentage elongation), and also exerts the same pressure as said main portion.

Such a tape therefore constitutes an extension of the therapeutic action of the stocking, and gives rise to a risk of strangulation, which although smaller than that associated with hosiery stockings is nevertheless sufficient for a stocking of that type to be considered as providing poor performance as a medical elastic stocking.

Document FR-A-2 302 054 describes an elastic stocking fitted with an elasticated garter band fixed to the main portion of the stocking by means of an overcast seam. The garter band is constituted by elasticated cloth covered on the inside over substantially its entire height by means of a grooved elastomer. Such a covering which is said to be non-slip, does not provide effective protection against slipping since, with the allowable amount of thickness (excessive-tightness would give rise to a rise of strangulation), it adheres insufficiently to the skin. In addition, that document gives no teaching on the choice of an elongation characteristic and/or on a special pressure to be exerted by the garter band, but gives teaching only with respect to avoiding the tourniquet effect at the seam securing said band so as to avoid marking the skin.

Finally, document U.S. Pat. No. 3,800,331 describes a stocking that applies uniform pressure (i.e. pressure that is not degressive) and that is fitted with an antislip band formed by alternating annular zones knitted with a springy elasticated thread, and transition zones having a vertical thread. It is specified that the diameter of the band is selected to be equal to or greater than the diameter of the main portion of the stocking in the vicinity of said band. Using such teaching that consists in selecting the length of the band (when flat) for the purpose of adjusting the pressure that is exerted, no attention is paid to the elongation characteristic thereof such that the tightness exerted by the band may be excessive. Doubtless that is the reason why such a stocking is usable only when made to measure, as is specified in the document.

As a subsidiary point, the antislip band includes projecting elasticated threads on its inside, and this constitutes a source of discomfort (in particular because the threads tweak hairs).

OBJECT AN BRIEF SUMMARY OF THE INVENTION

The invention seeks specifically to solve that problem by providing a remedial support appliance fitted with effective antislip means.

An object of the invention is to provide a remedial support appliance, in particular an elastic stocking, fitted with antislip means that are simultaneously effective, discrete, comfortable, and non-traumatic.

More particularly, the present invention provides a remedial support appliance for-medical use on a leg or an arm, comprising a main portion of elasticated knit serving to compress the limb on which the appliance is worn for the purpose of treating venous or lymphatic insufficiency, which main portion is extended upwards by an elasticated garter band, wherein the elasticated garter band is formed by an elasticated braid or an elasticated lace covered on the inside with a pattern made of an antislip material, the fibers constituting the braid or the lace of said garter band being selected in such a manner that said band presents an elongation characteristic [traction force as a function of percentage elongation] of a shallow slope and simultaneously exerts pressure on the limb in question that is less than the pressure exerted by the main portion in the vicinity of the garter band.

It is advantageous to observe that the characteristics of the garter band of the medical support appliance for medical use of the invention are completely opposite to those of an antislip band of hosiery stockings.

Preferably, the antislip pattern of the elasticated garter band is implemented in the form of at least one band, line, or succession of touching stitches, continuously disposed on and extending circumferentially around the inside periphery of said garter band, with the total height of the antislip pattern lying essentially in the range 1 cm to 6 cm.

By way of advantageous example, it is possible to provide that the antislip pattern is constituted by two superposed bands each about 1.5 cm high, the two bands being separated by an uncovered portion of the elasticated lace or braid that is about 1 cm high, it also being possible for said antislip pattern is to bemade of silicone or the like deposited continuously or discontinuously on the inside periphery of the elasticated garter band.

Also preferably, the fibers constituting the elasticated lace or braid are selected in such a manner that the elongation characteristic of the elasticated garter band corresponds, above an elongation of 15%, substantially to 10% elongation per Newton exerted in traction, and that the elasticated garter band exerts pressure on the limb in question that lies essentially in the range $0.1 P_0$ to $0.8 P_0$ where $P_0$ is the pressure exerted on the limb by the main portion of the appliance in the vicinity of said garter band.

It is then advantageous for the elasticated lace or braid of the elasticated garter band to be cut to a circumferential length that is determined as a function of various different sizes, in particular five sizes, and for the pressure exerted by said garter band to lie in a range that narrows with increasing size. In particular, the values of pressure exerted by the elasticated garter band lie preferably in the following ranges $0.2 P_0$ to $0.6 P_0$, $0.4 P_0$ to $0.75 P_0$, and $0.45 P_0$ to $0.8 P_0$ respectively for the three commonest sizes.

It is also advantageous for the elasticated lace or braid to be made from an elasticated fiber and from textile fibers of textured or continuous type. In particular, the elasticated fiber is an elasthanne or an elastodiene, and the textile fibers are made of polyamide, cotton or the like.

Finally, and preferably, the elasticated braid is woven or knitted.

BRIEF DESCRIPTION OF THE DRAWING

Other characteristics and advantages of the invention appear more clearly in the light of the following description and the accompanying drawing, relating to particular embodiments, and with reference to the figures, in which:

FIGS. 1 and 2 show two remedial support appliances of the invention, respectively in the form of a stocking and in the form of a sleeve, together with their elasticated garter bands for holding them up;

FIGS. 3a, 3b, and 3c are on a larger scale and show three examples of the way in which an antislip pattern can be provided on the inside periphery of the garter band; and FIG. 4 is a force/extension graph where the continuous line shows the shallow slope characteristic of the garter band of the invention, and where dashed lines and chain-dotted lines show the steep slope characteristics of two typical garter bands used as antislip systems in hosiery stockings.

MORE DETAILED DESCRIPTION

FIGS. 1 and 2 show two remedial support appliances of the invention and there can thus be seen a stocking 10 in FIG. 1 and a sleeve 15 in FIG. 2.

As is the usual practice in this art, each remedial support appliance for medical use 10 or 15 includes a respective main portion 11 or 16 of elastic knit, serving to compress the limb on which the appliance is worn in order to treat venous or lymphatic insufficiency, with the pressure applied decreasing from the bottom towards the top of the appliance.

In accordance with an essential feature of the invention, the main portion 11 or 16 of the remedial support appliance for medical use 10 or 15 is extended upwards by an elasticated i.e., elasticized garter band 20 whose particular structure is described below in detail, said elasticated garter band being capable of preventing the top portion of the support appliance 10 or 20 slipping, and consequently of avoiding creases in the appliance, while nevertheless keeping away from any risk of strangulation of the limb concerned that is being compressed. The elasticated garter band 20 is thus constituted by elasticated braid or elasticated lace which is covered, on the inside, with a pattern made of antislip material, and the fibers constituting the braid or the lace of said garter band are chosen so that said garter band has predetermined characteristics of flexibility and of pressure exerted.

FIGS. 3a, 3b, and 3c show three examples of possible ways in which the antislip pattern 23 can be disposed circumferentially on the inside periphery of the elasticated garter band 20.

Thus, in FIG. 3a there can be seen an elasticated braid 21 which is connected by circumferential stitching 22 to the main portion 11 or 16 of the support appliance concerned. In this case elasticated braid is shown, but in a variant it could naturally be constituted by elasticated lace. Naturally the elasticated garter band 20 which is shown only in part in the figure extends in practice all the way round the limb concerned. On the inside, as shown in FIG. 3a, the elasticated braid 21 is covered by a pattern 23 made of antislip material, said pattern being preferably made of silicone or the like, and being continuously deposited on the inside periphery of the elasticated garter band 20. In FIG. 3a, the antislip pattern 23 shown is constituted by two superposed bands 23.1 which are rectilinear in this case.

In FIGS. 3b and 3c, there can be seen two variants of said elasticated garter band 20, in which the antislip pattern 23 is respectively implemented in the form of successions of adjacent stitches 23.2 or of superposed wavy lines 23.3 which are deposited continuously. In the case comprising a succession of stitches, there can be seen a set of four lines of stitches 23.2, while in FIG. 3c, two superposed sinusoidal lines 23.3 are shown.

Tests performed by the Applicant have shown that it is advantageous to provide for the total height of the antislip pattern 23 on the elastic garter band 20 to lie preferably essentially in the range 1 cm to 6 cm. If the height of the band is too small, then there is a risk of obtaining a strangulation effect that is completely undesirable in the context of a remedial support appliance for medical use, while if its height is too great, then the elastic garter band becomes too uncomfortable and the patient would rather not wear the appliance in question.

For example, FIG. 3a shows two superposed bands 23.1 constituting the antislip pattern 23, where each band is about 1.5 cm high, and where the two bands are separated by a non-covered portion of the elasticated braid 21 that extends over a height of about 1 cm, such that the total height of the antislip pattern itself is about 3 cm. FIG. 3b shows a set of four superposed lines 23.2 constituted by successive sequences of touching stitches, with the height of each individual line being about 0.5 cm, thus giving the antislip pattern a height of about 2 cm. FIG. 3c shows two superposed sinusoidal lines 23.3 each having an individual height of about 0.5 cm such that the antislip pattern has a total height of about 1 cm.

Naturally other types of antislip pattern could be envisaged by modifying the examples described above, in particular discontinuous patterns in the form of strips or lines made up of disjoint lengths that extend circumferentially (thereby making it possible to apply a smaller tightening force to the limb concerned than that which is applied by continuous bands or lines).

The antislip pattern provided on the inside of the elasticated lace or braid applies, on its own, practically no return force when traction is exerted on the band. As a result, when considering the elongation characteristics of the elasticated garter band of the remedial support appliance of the invention, the characteristics looked for in said band must be provided by the fibers constituting the elasticated lace or braid in question.

In accordance with a characteristic of the invention, the fibers constituting the braid or lace of the elasticated garter band are selected in such a manner that said band presents an elongation characteristic of shallow slope and simultaneously exerts pressure on the limb concerned that is less than the pressure exerted by the main portion of the appliance in the vicinity of said garter band.

The elasticated garter band is thus quite different from bands used in the past as antislip means for hosiery stockings.

In order to understand better how significant these differences are both with respect to flexibility of the band and with respect to pressure exerted on the limb in question, there follow, solely by way of example, various comparisons between an elasticated garter band for a remedial support appliance for medical purposes of the invention and elasticated bands having the same dimensions but of the type used as antislip means for hosiery stockings.

We begin by investigating the elongation characteristic of the bands concerned by referring to FIG. 4.

FIG. 4 is an elongation graph showing variations in the traction force exerted on an elasticated band as a function of the elongation of said band. Percentage elongation $\Delta l$ relative to the initial (or rest) length of the band in question is plotted along the abscissa, while the traction force (in Newtons) exerted on said band is plotted up the ordinate. Using an elasticated garter band of the invention, a curve C is obtained in which the useful zone MN is linear and presents a shallow slope while traction is increased. When the applied force is released, the length of curve passes through a point P on its way back to the origin of the graph, because of the hysteresis in the elasticated band. It can thus be observed that the elongation characteristic of the elasticated garter band of the invention corresponds, starting from an elongation of 15% (point M) substantially to 10% of elongation per Newton exerted in traction.

The same FIG. 4 also shows two typical curves C' and C" relating to elasticated bands of conventional type as used in hosiery stockings. In each of these curves, there can be found an essentially linear useful zone M'N' or M"N", but the slopes in question are much steeper than the slope of a length MN corresponding to an elasticated band of the invention.

Because of the shallow slope of the elongation characteristic, the variations in pressure that are obtained within a given range of sizes are small, thereby obtaining for the patient a sensation of flexibility that enables a large amount of tolerance to be accommodated between dimensional variations of the limb in question as a function of the size of the remedial support appliance used (e.g. a small-sized ankle and a large-sized upper thigh), and also as a function of variations in the circumference of the limb (for example, it is known that the circumference of the thigh varies considerably while walking and during the day). It is thus possible to implement a remedial support appliance for medical use which is degressive with respect to the pressure with which it applies on the limb in question, in accordance with a predetermined law, and with the elasticated garter band that extends the top of the appliance having no effect on flexibility for a given size, while extending the degressive nature of the pressure that is exerted. In practice, the maximum pressure that is to be exerted at the top of the limb in question is determined as a function of the pressure exerted on the bottom portion thereof so as to obtain a desired therapeutic effect to counter venous or lymphatic insufficiency.

It should be observed that the above-mentioned shallow slope is, in particular, smaller than the slope of the elongation characteristic of the main portion of the stocking in the vicinity of the garter band, which slope complies, in practice, with the slope of the lengths M'N' or M"N" shown in FIG. 4.

The elasticated garter band of the remedial support appliance of the invention must also satisfy criteria concerning pressure exerted, insofar as the garter band must exert pressure on the limb in question that is less than the pressure exerted by the main portion of the remedial support appliance in the vicinity of said garter band, as mentioned above.

Tests performed by the Applicant tend to show that good results are obtained by selecting a pressure P essentially lying in the range $0.1 P_0$ to $0.8 P_0$ where $P_0$ is the pressure exerted on the limb by the main portion 11 or 16 in the vicinity of said garter band. In particular, the elasticated lace or braid 21 of the elasticated garter band 20 should have a circumferential length that is cut as a function of various different sizes, e.g. five sizes, and the pressure P exerted by said garter band then lies within a range that becomes narrower with increasing size.

For example, for the three commonest sizes in general use, i.e. sizes that correspond to respective circumferential measurements around the thigh of 46 cm to 48 cm, 49 cm to 53 cm, and 54 cm to 58 cm, the fibers constituting the elasticated lace or braid of the garter band are chosen in such a manner that the values of the pressure P exerted by said elasticated band lie preferably in the following ranges respectively: $0.2 P_0$ to $0.6 P_0$, $0.4 P_0$ to $0.75 P_0$, and $0.45 P_0$ to $0.8 P_0$ for the three above-mentioned sizes.

The elasticated lace or braid 21 is preferably made from an elasticated fiber and from textured or continuous type textile fibers. The elasticated fiber may be made of elasthanne which is an elastomer fiber constituted by at least 85% by mass of segmental polyurethane, or of elastodiene which is an elastomer fiber constituted by natural or synthetic polyisoprene, or else by one or more polymerized dienes with or without one or more vinyl monomers. By way of example, the elasticated fiber could be chosen to have a mass per unit length of 10 decitex to 160 decitex. The textile fibers are preferably selected to be made of polyamide, or cotton, or the like, said fibers being of textured or continuous type. In practice, the elasticated braid 21 is woven or knitted.

A remedial support appliance for medical use, in particular an elastic stocking or sleeve has thus been provided that is fitted with antislip means that are simultaneously effective, discrete, comfortable, and nontraumatic.

For legs, the invention makes it possible to wear elastic stockings that are more hygienic than tights, and that are in addition particularly suitable for the special case of pregnant women. Given that the comfort of the support appliance allows patients almost to forget that they are wearing an appliance, it is possible to prescribe them even in summertime. In a case of edema of the arm, the invention makes it possible to avoid the traumatic fastening system which constitutes a most important advantage for people who are already shocked by surgery of the breast or by cobalt therapy.

The invention is not limited to the embodiments described above, but on the contrary covers any variant that uses equivalent means to reproduce the essential characteristics specified above.

We claim:

1. A remedial support appliance for medical use on a leg or an arm, comprising a main portion of an elasticized knit serving to compress the limb on which the appliance is worn for the purpose of treating venous or lymphatic insufficiency, which main portion is extended upwards by an elasticized garter band, wherein the elasticized garter band is formed by an elasticized braid or an elasticized lace covered on the inside with a pattern made of an antislip material, the fibers constituting the braid or the lace of said garter band being selected in such a manner that said band presents an elongation characteristic of a shallow slope corresponding to a percentage elongation at least equal to 10% per Newton exerted in traction, wherein the elongation characteristic is defined as traction force as a function of percentage elongation and simultaneously exerts pressure on the limb that is less than the pressure exerted by the main portion in the vicinity of the garter band.

2. A remedial support appliance according to claim 1, wherein the antislip pattern of the elasticized garter band is constructed in the form of at least one band continuously disposed on and extending circumferentially around the inside periphery of said garter band, with the total height of the antislip pattern lying essentially in the range 1 cm to 6 cm.

3. A remedial support appliance according to claim 2, wherein the antislip pattern is constituted by two superposed bands each about 1.5 cm high, the two bands being separated by an uncovered portion of the elasticized lace or braid that is about 1 cm high.

4. A remedial support appliance according to claim 1, wherein the antislip pattern is made of silicone deposited on the inside periphery of the elasticized garter band.

5. A remedial support appliance according to claim 1, wherein the fibers constituting the elasticized lace or braid are selected in such a manner that the elongation characteristic of the elasticized garter band corresponds, above an elongation of 15%, substantially to 10% elongation per Newton exerted in traction, and that the elasticized garter band exerts pressure on the limb that lies essentially in the range $0.1 P_0$ to $0.8 P_0$ where $P_0$ is the pressure exerted on the limb by the main portion of the appliance in the vicinity of said garter band.

6. A remedial support appliance according to claim 5, wherein the elasticized lace or braid of the elasticized garter band is cut to a circumferential length that is determined as a function of a plurality of different sizes, and the pressure exerted by said garter band lies in a range that narrows with increasing size.

7. A remedial support appliance according to claim 6, wherein the values of pressure exerted by the elasticized garter band lie in the range of $0.2 P_0$ to $0.8 P_0$.

8. A remedial support appliance according to claim 1, wherein the elasticized lace or braid is made from an elasticized fiber and from textile fibers of textured or continuous type.

9. A remedial support appliance according to claim 8, wherein the elasticized fiber is an elasthanne or an elastodiene, and the textile fibers are made of polyamide, or cotton.

10. A remedial support appliance according to claim 8, wherein the elasticized braid is woven or knitted.

11. A remedial support appliance according to claim 1, wherein the antislip pattern of the elasticized garter band is constructed in the form of at least one line continuously disposed on and extending circumferentially around the inside periphery of said garter band, with the total height of the antislip pattern lying essentially in the range 1 cm to 6 cm.

12. A remedial support appliance according to claim 1, wherein the antislip pattern of the elasticized garter band is constructed in the form of a succession of touching stitches continuously disposed on and extending circumferentially around the inside periphery of said garter band, with the total height of the antislip pattern lying essentially in the range 1 cm to 6 cm.

* * * * *